US009809848B2

(12) United States Patent
Jones

(10) Patent No.: US 9,809,848 B2
(45) Date of Patent: Nov. 7, 2017

(54) SIMULTANEOUS DETECTION OF TARGET PROTEIN AND TARGET NUCLEIC ACIDS IN A SINGLE CELL

(71) Applicant: Fluidigm Corporation, South San Francisco, CA (US)

(72) Inventor: Robert C. Jones, Los Altos, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 14/775,960

(22) PCT Filed: Mar. 14, 2014

(86) PCT No.: PCT/US2014/028751
§ 371 (c)(1),
(2) Date: Sep. 14, 2015

(87) PCT Pub. No.: WO2014/144371
PCT Pub. Date: Sep. 18, 2014

(65) Prior Publication Data
US 2016/0024557 A1 Jan. 28, 2016

Related U.S. Application Data

(60) Provisional application No. 61/799,559, filed on Mar. 15, 2013.

(51) Int. Cl.
*C12Q 1/68* (2006.01)
*G01N 33/53* (2006.01)
*G01N 33/532* (2006.01)

(52) U.S. Cl.
CPC ............ *C12Q 1/686* (2013.01); *C12Q 1/682* (2013.01); *G01N 33/532* (2013.01); *G01N 2458/10* (2013.01)

(58) Field of Classification Search
CPC .... C12Q 1/682; C12Q 1/6844; C12Q 1/6846; C12Q 1/6851; C12Q 1/6853; C12Q 1/6855; C12Q 1/686
See application file for complete search history.

(56) References Cited

U.S. PATENT DOCUMENTS

| | | | |
|---|---|---|---|
| 7,723,123 | B1 | 5/2010 | Murphy et al. |
| 8,012,685 | B2 | 9/2011 | Shannon et al. |
| 2001/0014466 | A1 | 8/2001 | Lubenow et al. |
| 2008/0131883 | A1 | 6/2008 | Adams et al. |
| 2008/0145910 | A1 | 6/2008 | Ward et al. |
| 2010/0285447 | A1 | 11/2010 | Walsh et al. |
| 2011/0287436 | A1 | 11/2011 | Shannon et al. |
| 2015/0132743 | A1 | 5/2015 | Egidio et al. |

FOREIGN PATENT DOCUMENTS

| | | |
|---|---|---|
| CN | 101382552 | 3/2009 |
| WO | 93/06240 | 4/1993 |
| WO | 99/37806 A2 | 7/1999 |
| WO | 2008/016644 A1 | 2/2008 |
| WO | 2012/104261 A1 | 8/2012 |
| WO | 2013113699 | 8/2013 |
| WO | 2015035087 | 3/2015 |

OTHER PUBLICATIONS

Lundberg et al. "Homogeneous antibody-based proximity extension assays provide sensitive and specific detection of low-abundant proteins in human blood," Nucleic Acids Research, e-pub. Jun. 6, 2011, vol. 39, No. 15, p. e102, 8 pages.
Murakami et al. "Sensitive RNA detection by combining three-way junction formation and primer generation-rolling circle amplification," Nucleic Acids Research, e-pub. Nov. 29, 2011, 2012, vol. 40, No. 3, p. e22, 10 pages.
Wharam et al. "Specific detection of DNA and RNA targets using a novel isothermal nucleic acid amplification assay based on the formation of a three-way junction structure," Nucleic Acids Research, 2001, vol. 29, No. 11, p. 354, 8 pages.
International Search Report and Written Opinion dated May 5, 2014 for PCT Patent Application No. PCT/US2014/028751, 9 pages.
EP14763446.3 , "Extended European Search Report", dated Oct. 27, 2016, 10 pages.
Holland et al., "Detection of specific polymerase chain reaction product by utilizing the 5'-3' exonuclease activity of thermos aquaticus DNA polymerase", Proceeding of the National Academy of Sciences, vol. 88, Aug. 1991, pp. 7276-7280.
Blokzijl et al., "Protein biomarker validation via proximity ligation assays", Biochimica Biophysica Acta., vol. 1844, No. 5, 2014, pp. 933-939.
Chen et al., "Ionic strength-dependent persistence lengths of single-stranded RNA and DNA", Proc Natl Acad Sci USA, vol. 109, No. 3, Jan. 17, 2012, pp. 799-804.
Darmanis et al., "Simultaneous Multiplexed Measurement of RNA and Proteins in Single Cells", Cell Reports, vol. 14, No. 2, Jan. 1, 2016, pp. 380-389.
Efroni et al., "Global transcription in pluripotent embryonic stem cells", Cell Stem Cell., vol. 2, No. 5, May 8, 2008, pp. 437-447.
EP14842635.6 , "Extended European Search Report", dated Feb. 27, 2017, 9 pages.
Fernandez et al., "Establishment and characterization of cloned human thymic epithelial cell lines. Analysis of adhesion molecule expression and cytokine production", Blood, vol. 83, No. 11, 1994, pp. 3245-3254.
Fluidigm , "CI Single-Cell AutoPrep System", Available at URL: http://www.csbiotech.com.tw/upload/2013/01/20130109115744.pdf, 2012, pp. 1-4.
Genshaft et al., "Multiplexed, targeted profiling of single-cell proteomes and transcriptomes in a single reaction", Genome Biology, vol. 17, No. 1, Sep. 19, 2016, pp. 1-15.
Lee et al., "Inverted colloidal crystals as three-dimensional microenvironments for cellular co-cultures", J. Mater. Chem., vol. 16, 2006, pp. 3558-3564.

(Continued)

Primary Examiner — James Martinell
(74) Attorney, Agent, or Firm — Kilpatrick Townsend & Stockton LLP

(57) ABSTRACT

Methods and reagents for detection and analysis of nucleic acids are provided. The methods employ proximity extension assays for detection of a target nucleic acids of interest, e.g., a target RNA. The method can additionally be used in multiplex assays with a protein proximity extension assay to detect protein.

11 Claims, 1 Drawing Sheet

(56) References Cited

OTHER PUBLICATIONS

Magalhães et al., "Promiscuous gene expression in the thymus: the root of central tolerance", Clin Dev Immunol., vol. 13, No. 2-4, Jun.-Dec. 2006, pp. 81-99.
PCT/US2014/054146 , "International Search Report and Written Opinion", dated Dec. 23, 2014, 15 pages.
PCT/US2014/054146 , "Invitation to Pay Additional Fees", dated Oct. 28, 2014, 2 pages.
Peterson et al., "Transcriptional regulation by AIRE: molecular mechanisms of central tolerance", Nat Rev Immunol., vol. 8, No. 12, Dec. 2008, pp. 948-957.
Ruff et al., "Systems Biology Using Multilevel Data from Single Cells", Available at URL:https://www6.inra.fr/microgenomics . . ./Microgenomics+2014+RUFF+FINAL.pdf , 2014, p. 1.
Schallmeiner et al., "Sensitive protein detection via triple-binder proximity ligation assays", Nat Methods, vol. 4, No. 2, 2007, pp. 135-137.
Stahlberg et al., "Quantitative PCR analysis of DNA, RNAs, and proteins in the same single cell", Clinical Chemistry, vol. 58, Issue 12, Dec. 2012, pp. 1682-1691.
Tavoosidana et al., "Multiple recognition assay reveals prostasomes as promising plasma biomarkers for prostate cancer", Proc Natl Acad Sci USA., vol. 108, No. 21., May 24, 2011, pp. 8809-8814.
Wu et al., Thymic epithelial cells use macroautophagy to turn their inside out for CD4 T cell tolerance, Autophagy, vol. 9, No. 6, 2013, pp. 931-932.
"Non-Final Office Action", U.S. Appl. No. 14/477,721, Jun. 22, 2017, 18 pages.
Linke , "Detergents: an overview", Methods in Enzymology, vol. 463, 2009, pp. 603-617.
Wang et al., "Performance of nanoliter-sized droplet-based microfluidic PCR", Biomed Microdevices, vol. 11, issue 5, May 28, 2009, pp. 1-19.

SIMULTANEOUS DETECTION OF TARGET PROTEIN AND TARGET NUCLEIC ACIDS IN A SINGLE CELL

CROSS-REFERENCE TO RELATED APPLICATIONS

This application is a US National Phase of PCT Application No. PCT/US2014/028751, filed on Mar. 14, 2014, which claims benefit of U.S. provisional application No. 61/799,559, filed Mar. 15, 2013, herein incorporated by reference for all purposes.

FIELD OF THE INVENTION

The invention relates to an amplification-based detection system that is sufficiently sensitive for detection of nucleic acids, e.g., RNA in a single cell. The method can be used in conjunction with a proximity extension assay for protein detection to provide a multiplex assay to detect both nucleic acids and proteins.

BACKGROUND

Detection and quantification of protein and nucleic acids from individual cells is desirable, but difficult to achieve because of the minute amount of material present in a single cell. Further, unlike bulk samples, a single cell cannot be divided into portions to separately analyze protein and nucleic acid levels. Although single molecule detection techniques or mass spectrometry may provide methods for achieving single cell analysis, such methods are expensive. Recently, an assay, the Proximity Extension Assay (PEA) has been developed that is sensitive enough to detect picogram quantities of protein (see, e.g., Lundberg et al., *Nucl. Acids Res.* 2011 August; 39(15):e102; epub 2011 Jun. 6, incorporated by reference herein). In one approach, the PEA employs a pair of antibodies, each having a oligonucleotide attached to it. The oligonucleotides contain regions that complement one another. When the antibodies bind to a target protein, the oligonucleotides are in close enough proximity so that complementary regions from each oligonucleotide hybridize to one another. The addition of a DNA polymerase results in extension of the hybridized oligonucleotides. The extension products can then be detected or quantified.

BRIEF DESCRIPTION OF THE INVENTION

In various aspects, the invention includes, but is not limited to, the following embodiments.

In one aspect the invention provides a method of detecting a target nucleic acid, typically RNA, in a sample, the method comprising (a) incubating in a reaction mixture: i) a sample comprising a target nucleic acid; and ii) a pair of proximity probes comprising a first and second probe, where: the first probe comprises a target binding (TB) segment that hybridizes to a first target (T) segment of the target nucleic acid, and an interacting (I) segment at the 3' end of the probe, wherein the I segment is complementary to an I segment at the 3' end of the second probe; and the second probe comprises a TB segment that hybridizes to a second, non-overlapping T segment of the target nucleic acid that is in close proximity to the first T segment, and an I segment at the 3' end, wherein the 3' sequence is complementary to the I segment of the first probe, wherein the reaction mixture is incubated under conditions in which the TB segment of the first probe hybridizes to the first T segment of the target nucleic acid and the TB segment of the second probe hybridizes to the second T segment of the target nucleic acid, thereby allowing the I segment of the first probe to hybridize to the I segment of the second probe to form a duplex comprising the I segments of the first and second probe;

(b) adding a DNA polymerase and maintaining the reaction mixture under conditions in which the first and/or second probe is extended to obtain a first extended product;

(c) amplifying the extended product, or a subregion thereof, in an amplification reaction mixture comprising a pair of amplification primers that amplify the first extended product, or subregion thereof;

(d) detecting the amplicon obtained in (c).

In some embodiments, the step of detecting the amplicon comprises quantifying the amplicon, e.g., using a qPCR reaction.

In some embodiments, the sample is a single cell.

In some embodiments, one of the members of the proximity pair is blocked at the 3' end so that only one probe is extended in step (b).

In some embodiments, the DNA polymerase employed in the extension step has 3' exonuclease activity. In some embodiments, the polymerase used for the amplification step is different from the polymerase used for the extension step. For example, the polymerase used for the amplification step may be thermostable whereas the polymerase used for the extension step may not be thermostable.

In some embodiments, the method further comprises detecting a target protein in the sample. In such embodiments, the method further comprises:

incubating the sample in the reaction mixture of (a) with a pair of protein-detecting proximity probes comprising a first and a second protein-detecting proximity probe where:

the first protein-detecting probe comprises a first antibody that binds to the target protein joined to a first polynucleotide that comprises an I segment at the 3' end that is complementary to an I segment on the 3' end of the second probe; and the second protein-detecting probe comprises a second antibody that binds to the target protein joined to a second polynucleotide that comprises an I segment complementary to the I segment at the 3' end of the first polynucleotide;

wherein binding of the first antibody to the target protein and binding of the second antibody to the target protein allows the I segment of the first protein proximity probe to hybridize to the I segment of the second protein proximity probe to form a duplex which is extended in step (b) to provide a second extended product;

amplifying the second extended product, or subregion thereof, in the amplification reaction of (c) using a set of primers that amplify the second extended product or subregion thereof; and detecting the amount of amplicon from amplification of the second extended product or subregion thereof.

In some embodiments, the step of detecting the amount comprises quantifying the amount of amplicon, e.g., using a qPCR reaction.

In some embodiments, the reaction is a multiplex reaction in which multiple RNAs are detected.

In a further aspect, the invention includes a use of a proximity probe pair for the detection/quantification of a target nucleic acid in a sample; or a use of proximity probe pairs for detection/quantification of target nucleic acids and proteins in a sample. In some embodiments, the invention provides a use of a proximity probe pair for the detection/quantification of a target nucleic acid in a sample; or a use of proximity probe pairs for detection/quantification of target nucleic acids and proteins in a sample, wherein one of the members of the proximity probe pair is blocked.

DETAILED DESCRIPTION

1. Definitions and Terminology

Figure 1:
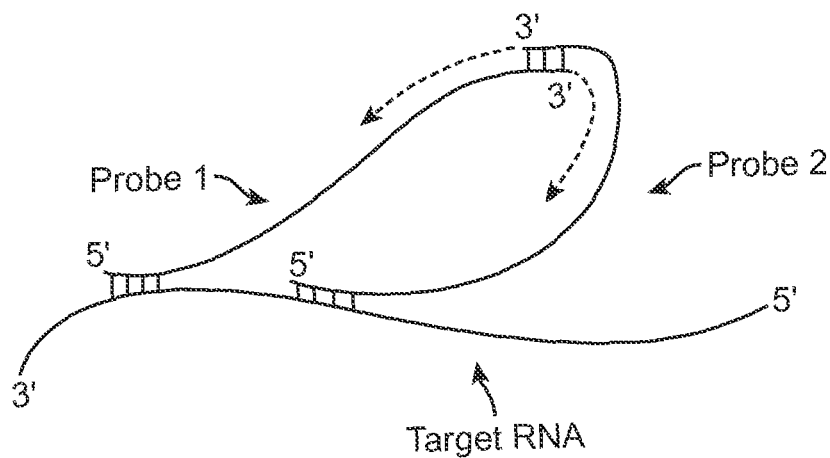
FIG. 1 illustrates an embodiment of a nucleic acid proximity extension assay to detect a target RNA. In this embodiment, the 3' end of each member of the probe pair is extendible.
Figure 2:
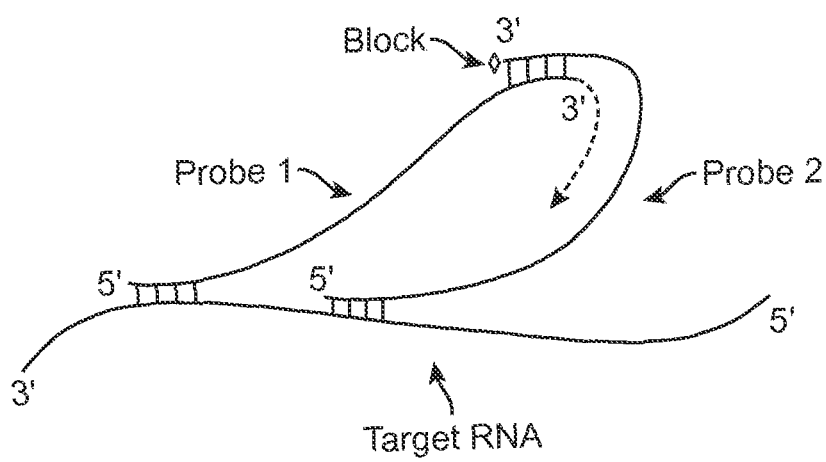
FIG. 2 illustrates another embodiment of a nucleic acid proximity extension assay to detect a target RNA. In this embodiment, the 3' end of one of the probes is blocked.

As used herein, a "sequence" means a nucleic acid base sequence of a polynucleotide. Unless otherwise indicated or apparent from context, bases or sequence elements are presented in the order 5' to 3' as they appear in a polynucleotide.

A "polynucleotide" or "nucleic acid" includes any form of RNA or DNA, including, for example, genomic DNA; complementary DNA (cDNA), which is a DNA representation of messenger RNA (mRNA), usually obtained by reverse transcription of mRNA; and DNA molecules produced synthetically or by amplification. Polynucleotides may include chimeric molecules and nucleic acids comprising non-standard bases (e.g., inosine). Polynucleotides may be single-stranded or double-stranded.

The term "oligonucleotide" is used herein to refer to a nucleic acid that is relatively short, generally shorter than 200 nucleotides, more particularly, shorter than 100 nucleotides or shorter than 50 nucleotides. Typically, oligonucleotides are single-stranded DNA molecules.

A "target polynucleotide" or "target nucleic acid" is a polynucleotide that comprises a target sequence. In a double-stranded target polynucleotide the target sequence is on one strand and the complement of the target sequence is on the other strand. A "target RNA" is an RNA that comprises a target sequence.

The term "segment," refers to a sequence or subsequence in a polynucleotide, such as a segment having a particular function, e.g., probe-binding segment, primer-binding segment, indexing sequence, also referred to herein as a "tag sequence", and others listed herein. Individual segments may have any length consistent with their intended function, such as, without limitation, lengths in the range of 10-100 nucleotides, 10-70 nucleotides, 14-50 nucleotides, and 14-35 nucleotides.

A "target sequence" is a nucleic acid sequence detected in an assay. In most cases a target sequence of interest is predefined (i.e., sequence is known prior to analysis). In other cases the complete target sequence is not known, but is defined as the sequence that is amplified by primers of known sequence. A target sequence may be found in DNA (including genomic, mitochondrial, viral, synthetic and cDNA), in RNA, or in amplifiable synthetic analogs thereof.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. A "complement" may be an exactly or partially complementary sequence. Complementarity between two single-stranded nucleic acid molecules may be "partial," in which only some of the nucleotides bind, or it may be complete when total complementarity exists between the single-stranded molecules. Two oligonucleotides are considered to have "complementary" sequences when there is sufficient complementarity that the sequences hybridize (forming a double stranded region) under assay conditions. The degree of complementarity between nucleic acid strands has significant effects on the efficiency and strength of hybridization between nucleic acid strands. Two sequences that are partially complementary may have, for example, at least 90% identity, or at least 95%, 96%, 97%, 98%, or 99% identity sequence over a sequence of at least 7 nucleotides, more typically over a sequence of 10-30 nucleotides, often over a sequence of 14-25 nucleotides, and sometimes over a longer sequence (e.g., 26-100 nucleotides in length). It will be understood that the 3' base of a primer sequence will desirably be perfectly complementary to corresponding bases of the target nucleic acid sequence to allow priming to occur. A first sequence or segment is "substantially complementary" to a second sequence of segment when a polynucleotide consisting of the first sequence is sufficiently complementary to specifically hybridize to a polynucleotide consisting of the second sequence. For illustration, hybridization conditions are salt concentrations less than about 1.0 M sodium ion, typically about 0.01 to 1.0 M sodium ion at pH 7.0 to 8.3, and temperatures at least about 30° C. for polynucleotides 10 to 50 nucleotides in length and at least about 60° C. for longer probes (e.g., greater than 50 nucleotides). Typically, specific hybridization will occur when there is at least about 55% base complementary over a stretch of at least 14-25 nucleotides, preferably at least 65%, more preferably at least 75%, more preferably at least 85%, more preferably at least 90%, and most preferably at least 95%. The prime symbol ['] is used to indicate a perfectly or substantially complementary sequence.

The terms "anneal", "hybridize" or "bind," in reference to two polynucleotide sequences, segments or strands, are used interchangeably and have the usual meaning in the art. Two complementary sequences (e.g., DNA and/or RNA) anneal or hybridize by forming hydrogen bonds with complementary bases to produce a double-stranded polynucleotide or a double-stranded region of a polynucleotide.

Two sequences or segments in a polynucleotide are "adjacent" or "contiguous" if there is no intervening sequence or non-nucleotide linker separating them. In some contexts, "non-adjacent" refers to two probe-binding sequences separated from each other by an intervening target sequence.

A "primer" is an oligonucleotide or polynucleotide comprising a sequence that is complementary to, and capable of hybridizing to, a target sequence, or the complement thereof. In general, "primer" means an "extendible primer" that can prime template-dependent DNA synthesis. In some cases a primer is extended by a DNA-dependent DNA polymerase.

A proximity probe can include a "nucleotide tag". The term "nucleotide tag" is used herein to refer to a predetermined nucleotide sequence that is incorporated into a proximity probe to facilitate identifying the target molecule in a multiplex action.

A proximity probe typically comprises DNA, but may also include polyribonucleotides (containing D-ribose), and any other type of nucleic acid that is an N- or C-glycoside of a purine or pyrimidine base, as well as other polymers containing nornucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

The terms "multiplex" and "multiplexing" refer to assays in which two or more primer sets are used to amplify two or more distinct target sequences in the same amplification reaction mixture.

As used herein, "amplification" of a nucleic acid sequence has its usual meaning, and refers to in vitro techniques for enzymatically increasing the number of copies of a target sequence. Amplification methods include both asymmetric methods (in which the predominant product is single-stranded) and conventional methods (in which the predominant product is double-stranded).

The terms "amplicon" and "amplification product" are used interchangeably and have their usual meaning in the art. The grammatically singular term, "amplicon," can refer to many identical copies of an amplification product. Moreover, reference to an "amplicon" encompasses both a molecule produced in an amplification step and identical molecules produced in subsequent amplification steps (such as, but not limited to, amplification products produced in subsequent rounds of a PCR amplification). Moreover, the term "amplification may refer to cycles of denaturation, annealing and extension, and does not require geometric or exponential increase of a sequence.

A "amplification reaction mixture" is the solution in which an amplification reaction takes place and may comprise one or more of target polynucleotides, primers, polymerase, ligase, amplification reagents, amplicons, buffering agents, nuclease inhibitors, divalent cations, dNTPs, and/or other components known in the art for amplification.

The term "qPCR" is used herein to refer to quantitative real-time polymerase chain reaction (PCR), which is also known as "real-time PCR" or "kinetic polymerase chain reaction."

As used herein, a "sample" refers to a composition containing a target polynucleotide. A "sample" may also contain a target protein. Exemplary samples include cells and cell lysates eukaryotic cells, human cells, animal cells, plant cells, stem cells, blood cells, lymphocytes, bacterial cells, recombinant cells and cells infected with a pathogen, tissue samples), viruses, environmental samples (e.g., water samples), food samples, forensic samples, plant samples, blood samples and the like. "Cell lysates" includes partially purified cell fractions.

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

2. Overview

In one aspect, the invention provides proximity extension methods for detecting a target nucleic acid in a sample. The method is typically used concurrently with a proximity extension assay for detecting levels of protein in the same sample. Typically, the target nucleic acid that is detected is an RNA. In some embodiments, the target may be single-stranded DNA, such as a single-stranded DNA virus.

In some embodiments, a target nucleic acid (e.g., RNA) is detected in a sample by a process in which a pair of proximity probes are hybridized to the target nucleic acid (e.g., RNA). Each member of a pair of proximity probes ("PPP") comprises a target binding segment ("TB" segment), often at or near the 5' end of the probe, that hybridizes to a predefined segment of the target nucleic acid ("T" segment). Each member of a PPP comprises an interaction segment ("I segment"), often at or near the 3' end of the probe, where the interaction segment of one member of the PPP is complementary to the interaction segment present in the other member of the PPP. The sequences of the proximity probes are selected or designed so that TB segments in each member of the proximity probe pair bind to different regions of the target nucleic acid (i.e., different, nonoverlapping, T segments), where the T segments are located in sufficiently close proximity, and the PPP's have sufficient length, so that the I segments can interact when the proximity probes are hybridized to the target RNA.

Binding of the probes to the target nucleic acid allows the I segments of the PPP to hybridize. A DNA polymerase is then added that extends the hybridized probes at their 3' ends, extending the portion of the PPP dimer that is double stranded. Hybridization of the I segments and extension of the duplex results in an extended product that can then be detected in an amplification reaction. Typically, each member of the proximity probe pair also comprises an amplification primer binding site (APBS) segment. Generally, each of the two probes of a PPP have a different APBS. Thus, when the proximity probes are hybridized via their I segments and extended by the polymerase, a double-stranded (or partially double-stranded) polynucleotide is generated, having a pair of APBSs. It will be recognized that each proximity probe has a single APBS, and the extension step results in a polynucleotide with both APBSs.

The methods of the invention can be conveniently used in a multiplex assay format. For example, if two or more target molecules, e.g., two or more target nucleic acids such as two different RNA targets, are to be detected, the products can be detected in a single reaction using multiple pairs of proximity probes, each of which forms an extension product that is unique. Similarly, when a nucleic acid, e.g., RNA, and a protein are to be detected in the same reaction, proximity probe pairs for the nucleic acid and protein, each of which forms a unique extension product, are used concurrently in a singled reaction. An assay of the invention can thus be readily multiplexed to evaluate the presence or amounts of multiple target molecules in a sample.

Amplification primers are used to amplify the extended product. The determination of the presence, absence, quantity, or relative amount of the amplified product is indicative of the presence, absence, quantity, or relative amount of the target sequence in the initial sample.

In some embodiments, the amount of extended product quantified in a qPCR reaction. A variety of other amplification systems may be used, as discussed below.

The methods for detecting a target nucleic acid, e.g., RNA, may also be used in conjunction with a proximity extension assay that detects protein present in a sample, as further detailed below.

3. Nucleic Acid Proximity Probe Pairs

This invention employs a proximity probe pair to detect a target nucleic acid, typically a target RNA, such as an mRNA. In other embodiments, a proximity probe pair can be used to detect a target DNA, such as viral DNA that may be present in a sample. Each member of the proximity probe pair comprises the following regions: a TB segment, an I segment, and an APBS segment. The TB segment is complementary to and binds a T segment of the target nucleic acid sequence. One member of the proximity probe pair binds to T segment on the target nucleic acid and the other member binds to a different, non-overlapping T segment on the target nucleic acid. The sites are in close proximity, i.e., such that hybridization of the TB regions to the target nucleic acid allows the complementary I regions to hybridize. Typically the probe binding sites are separated by fewer than 100 bases, often fewer than 50 bases, e.g., 40, 30, 20, or 15 nucleotides or less. In some embodiments two sequences or segments in a polynucleotide are considered to be "in close proximity" when they are separated by from 10 to 50 bases.

The TB segment of a proximity probe is located at or near the 5' end of the probe. For example, the TB segment may be positioned within 2-10 nucleotides of the nucleotide at the 5' end of the proximity probe. The size of the TB segment typically ranges anywhere from 10 to 100 nucleotides in length. In some embodiments, the TB segment is less than 50 nucleotides in length, and may be less than 20 or 10 nucleotides in length. For example, a TB segment may be from 5 to 20 or 10 to 40 nucleotides in length. These ranges are illustrative guidelines but are not intended to limit the invention.

The I region of a proximity probe is located at or near the 3' end of the probe such that the I region is available to hybridize to the complementary I region of the other member of the probe pair when the proximity probe pairs are hybridized to the target nucleic acid. In typical embodiments, an I segment is designed such that upon hybridization with the I segment of the other member of the proximity pair, there are no 3' non-base-paired nucleotides. However, other embodiments are also contemplated. For example, the 3' end, i.e., that has the free 3' hydroxyl group, of one of the proximity probes may not be included in the I segment that binds to the complementary I segment of the other member of the proximity probe pair, thus leaving non-base-paired nucleotides at the 3' end. Use of a polymerase having a 3' exonuclease activity will permit the extension of the probe that has the 3' non-based-paired nucleotides. In other embodiments, only one of the probes may be extended. Thus, a probe may be designed to have non-base-paired nucleotides at the 3' end. In some embodiments, one of the probes may be modified at the 3' end to prevent extension.

Typically, the I segment is less than 20 nucleotides in length. For example, the I segment may be from 6 to 12 nucleotides in length, e.g., 6, 7, 8, 9, 10, 11 or 12 nucleotides in length.

In typical embodiments, each member of the proximity probe pair also comprises an amplification primer binding site. Upon extension of the proximity probes, polynucleotide molecules in which both APBS sequences are present are produced. Extended polynucleotides having both amplification primer binding sites permits the amplification of the extension product using amplification primers that bind to the primer binding site. Alternatively, one member of the proximity probe pair may have an amplification primer binding site. A second amplification primer binding site, may for example, be created upon hybridization of the I regions of the proximity probes. In other embodiments only one member of the proximity probe pair may be extended. The extended probe can comprise two amplification primer binding sites to permit amplification of the extended product.

Probes are typically designed to avoid areas of secondary structure in the RNA. For example, one of skill can use known computer programs to provide a model of a structure of a target RNA. The TB region of the probe may then be designed to avoid regions of secondary structure such as hairpins, stems, and the like. Probes that are complementary to a target RNA segment can be designed using software readily available in the art, e.g., Primer 3 (Whitehead Institute for Biomedical Research).

In some embodiments, one of the members of the probe pair may be blocked to prevent extension. For example, one of the probes may have a modified base at the 3' end that prevents extension of the probe. In some embodiments, the 3' nucleotide may be phosphorylated. In other embodiments, the 3' end may have a modified nucleotide such as a thiophosphate-modified nucleotide, a 2'-OMe-CE phosphoramidite-modified nucleotide, or another extension-blocking nucleotide known in the art. In some embodiments, one or more nucleotides that prevent extension of a probe may be located upstream of the 3' end such that extension does not occur beyond that point. For example, a linker may be used to block extension of the probe.

The concentration of probes added to the reaction mixture to hybridize to target RNA is typically in the range of 1 nM to 100 nM. The time and temperature of incubation of the proximity probes with the sample can vary, depending on the particular probes used. The time should be sufficient so that the probes bind to the target nucleic acid and that the 3' ends hybridize. In illustrative embodiments, the time of incubation may be from anywhere from about 10 minutes to about 1-2 hours, or longer, e.g., 12 to 24 hours. The temperature at which the reaction is conducted can vary, depending on the probes employed and depending on whether other molecules, such as protein, are also detected in a multiplex assay. When only RNA is detected, typical incubations temperatures of the probe with the target can range from about 55° C. to about 70° C. Often, the incubation temperature is from about 60° C. to about 70° C., e.g., the incubation temperature is 61° C., 62° C., 63° C., 64° C. 65° C., 66° C., 67° C., 68° C., 69° C., or 70° C. When the assay is a multiplex assay that also detects protein, incubations temperatures are typically lower, for example from about 35° C. to about 45° C. In some embodiments, the temperature is in a range from about 37° C. to about 42° C. Illustrative reaction conditions for a multiplex reaction comprising detecting both target RNA and a target proteins comprise a probe concentration of 1 nM and incubation at 37° C. for one hour. Illustrative reaction conditions for detecting target RNA only comprise a probe concentration of 1 nM and incubation at 65° C. for 18 to 24 hours.

In some embodiments, the reaction additionally comprises components that can stabilize probe:RNA hybridization. An example of such a component is RNase H in which the RNase activity has been inactivated, or a single-stranded nucleic acid binding protein us as T4 gp32.

4. Extension Reaction

The extension reaction is typically carried out after the hybridization of the probes to the target molecules. Reagents such as nucleotides and a DNA polymerase are included in the extension reaction. Any DNA polymerase can be used. In some embodiments the DNA polymerase has 3' exonuclease activity. Examples of such polymerases include T4 DNA polymerase, T7 DNA polymerase, Phi29 (Φ29) DNA polymerase, DNA polymerase I, Klenow fragment of DNA polymerase I, *Pyrococcus furiosus* (Pfu) DNA polymerase, and *Pyrococcus woesei* (Pwo) DNA polymerase.

In other embodiments, a DNA polymerase that lacks 3' to 5' exonuclease activity may be employed. Such polymerases include polymerases such as Taq or ΔTaq polymerase.

The temperature at which the extension reaction is conducted depends on the nature of the polymerase employed. For example, reactions employing thermostable polymerases may be conducted at temperatures above 40 degrees Celsius. A temperature is employed, however, that allows the hybridized proximity probes to remain hybridized to the target nucleic acid and for the 3' end of the probes to stably hybridize.

The polymerase may be added to the assay along with the proximity probes or may be added following addition of the proximity probes. In some embodiments, the polymerase is added after a period of incubation of the proximity probes with the target polynucleotide.

5. Protein-Detecting Proximity Probe Pairs

In some embodiments, the detection of a target nucleic acid of interest, e.g., an RNA of interest, is performed simultaneously with detection of a protein of interest in the same reaction mixture. Accordingly, in some embodiments, the method comprises performing a proximity extension assay as described herein for detecting one or more specific RNAs and performing a proximity extension assay to detect one or more specific proteins. Proximity extension assays for detecting proteins are well known in the art (see, for example, Lundberg et al. *Nucl. Acids Res.* 39: e102, 2011; and WO2012/104261, each of which is incorporated by reference) and any such assay can be used.

In an illustrative assay that can be used in a multiplex assay with a nucleic acid proximity extension assay, a protein proximity probe pair, i.e., a proximity probe pair for detecting a protein of interest, comprises one probe that includes a nucleic acid binding segment (i.e., an I segment) linked to an antibody that binds to the protein of interest. The second probe in the pair includes a nucleic acid binding segment, (i.e., an I segment) that is complementary to the I segment of the first probe and is also linked to an antibody that binds to the target protein of interest. Upon binding of the antibodies to the target protein, the I segments hybridize.

The antibodies used for the protein proximity probes may be polyclonal or monoclonal antibodies, or fragments of antibodies. Further, the antibodies linked to each member of the protein proximity probe pair may have the same binding specificity or differ in their binding specificities. The present invention further contemplates use of variations of this assay, e.g., that are described in WO2012/104261. For example, the probes may each be linked to their respective antibody at the 5' end, or one probe may be linked at the 5' end and the other at the 3' end.

As noted above, upon binding of the antibodies of the protein proximity probe pair to the target protein, the 3' ends hybridize to form a double-stranded nucleic acid that has at least one 3' OH that can be extended by a polymerase as described above. As in the case of the nucleic acid proximity probe pair (for detecting the nucleic acid of interest, e.g., an RNA of interest), the proximity probes for the protein hybridize such that a unique sequence is created to serve as a sequence tag, which can be used as an identifier.

The extension reaction is performed at a temperature appropriate for the selected polymerase and under conditions in which the antibodies remain bound to the target proteins such that the 3' complementary ends of the probe pairs can hybridize. In an assay in which both nucleic acid proximity probe pairs and protein proximity probe pairs are used to detect a target nucleic acid and a target protein in the same reaction, the extension reaction is performed at a temperature appropriate for the selected polymerase and under conditions in which the T segments of the nucleic acid proximity probes remain bound to the target nucleic acid and the antibodies for the protein proximity probes remain bound to the target proteins so that for each of the proximity probe pairs, the 3' complementary segments can hybridize.

6. Amplification and Detection of Amplified Products

The extended products obtained from the extension reactions are subjected to an amplification reaction to obtain an amplified product that can be detected and quantified, as desired. Design parameters of various amplification reactions are well known. Examples of references providing guidance are provided below. In some embodiments the amplification reaction uses the same polymerase that is used in the extension assay, optionally without addition of more polymerase. In some embodiments the amplification reaction uses a polymerase that is different from the polymerase used for the extension assay. For example, in some embodiments, a polymerase having a 3' exonuclease activity may be used in the extension reactions and a Taq polymerase may be used in the amplification reaction.

In some embodiments, an amplification reaction may employ a hot-start polymerase. For example, a recombinant Taq DNA polymerase complexed with an antibody that inhibits polymerase activity at ambient temperatures may be used. The polymerase is active after a PCR denaturation step.

Any method of detection and/or quantitation of nucleic acids can be used in the invention to detect and/or quantify amplification products. In particular embodiments, real-time quantification methods are used. For example, "quantitative real-time PCR" methods can be used to determine the quantity of an amplified product present in a sample by measuring the amount of amplification product formed during the amplification process itself. This method of monitoring the formation of amplification product involves the measurement of PCR product accumulation at multiple time points. The amount of amplified product reflects the amount of target nucleic acid or target protein present in the sample.

Fluorogenic nuclease assays are one specific example of a real-time quantitation method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al, 1996, Real-time quantitative PCR Genome Res. 6:986-94, each incorporated herein by reference in their entireties for their descriptions of fluorogenic nuclease assays. It will be appreciated that while "TaqMan® probes" are the most widely used for qPCR, the invention is not limited to use of these probes; any suitable probe can be used.

Other detection/quantitation methods that can be employed in the present invention include FRET and template extension reactions, molecular beacon detection, Scorpion detection, and Invader detection.

FRET and template extension reactions utilize a primer labeled with one member of a donor/acceptor pair and a nucleotide labeled with the other member of the donor/acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al. (1998) Nat. Biotechnol. 16: 359-363; Tyagi, and Kramer (1996) Nat. Biotechnol. 14: 303-308; and Tyagi, et al. (1998) Nat. Biotechnol. 16:49-53, [0124] The Scorpion detection method is described, for example, by Thelwell et al. (2000) Nucleic Acids Res., 28: 3752-3761 and Solinas et al. (2001) Nucleic Acids Res., 29(20): e96. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase. [0125] Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal.

As noted above, various amplification and reaction methods may be used to detect the extended product. Thus, amplification according to the present invention encompasses any means by which at least a part of the extended product is copied, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(I):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth international Symposium on Human identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Add Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2): 165-74, Schweitzer et al., Curr Opin Biotechnol. 2001 February; 12(I):21-7, U.S. Pat. No. 5,830,711, U.S. Pat. No. 6,027,889, U.S. Pat. No. 5,686,243, PCT Publication No. WO0056927A3, and PCT Publication No. WO9803673A1.

As used herein, the term "amplification" includes isothermal amplification methods. Isothermal amplification uses a constant temperature rather than cycling through denaturation and annealing/extension steps. Some means of strand separation, e.g., an enzyme, is used in place of thermal denaturation. Examples of isothermal amplification include: hyperbranched strand displacement amplification (Groathouse, N., et al. (2006) "Isothermal Amplification and Molecular Typing of the Obligate Intracellular Pathogen *Mycobacterium leprae* Isolated from Tissues of Unknown Origins" J. Clin. Micro. 44 (4): 1502-1508); helicase-dependent amplification (Vincent. M., et al. (2004) "Helicase-dependent isothermal DNA amplification" EMBO Rep. 5 (8): 795-800); multiple displacement amplification (MDA; Luthra, R., and Medeiros, J. (2004) "Isothermal Multiple Displacement Amplification" J Mol Diagn. 6 (3): 236-242); loop-mediated isothermal amplification (Notomi, T., et al. (2000) Nucleic Acids Research 28 (1); PAN-AC (David, F. and Turlotte, E., (1998) "An Isothermal Amplification Method" C.R. Acad. Sci Paris, Life Science 321 (1); 909-14); strand displacement amplification (SDA; Nycz, C, et al. (1998) Analytical Biochemistry 259 (2): 228-234); rolling circle amplification (RCA; Lizardi, P., et al., (1998) "Mutation detection and single-molecule counting using isothermal rolling-circle amplification" Nature Genetics 19: 225-232); nucleic acid strand-based amplification (NASBA; Van Der Vliet, G., et al. (1993) "Nucleic acid sequence-based amplification (NASBA) for the identification of mycobacteria" Journal of General Microbiology 139 (10): 2423-2429; and recombinase polymerase amplification (U.S. Pat. Nos. 7,485,428; 7,399,590; 7,270,981; and 7,270,951, each of which is incorporated by reference in its entirety and specifically for its description of recombinase polymerase amplification).

In embodiments in which fluorophores are used as labels, many suitable fluorophores are known. Examples of fluorophores that can be used include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, 6-Fam™ are all available from Applied Biosystems, Foster City, Calif.).

In embodiments in which quenchers are also used for detection of amplified products, useful quenchers include, but are not limited to tetramethylrhodamine (TAMRA), DABCYL (DABSYL, DABMI or methyl red) anthroquinone, nitrothiazole, nitroimidazole, malachite green, Black Hole Quenchers®, e.g., BHQ1 (Biosearch Technologies), Iowa Black® or ZEN quenchers (from Integrated DNA Technologies, Inc.), TIDE Quencher 2 (TQ2) and TIDE Quencher 3 (TQ3) (from AAT Bioquest).

PCR and fluorescence detection can conveniently be performed using a system such as the BioMark™ System (Fluidigm Corporation, South San Francisco).

7. Samples

Any target nucleic acid can be detected using the proximity extension probe assays of the invention. In typical embodiments, the target nucleic acid is an RNA molecule. The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli. In some embodiments, the methods comprises concurrent detection of both RNA and protein targets is a sample using a nucleic acid proximity extension assay as described herein and a protein proximity extension assay Samples comprising a nucleic acid, e.g., RNA, or nucleic acid and protein of interest can be obtained from biological sources and prepared using conventional methods known in the art. In particular, samples to be analyzed in accordance with the methods described herein obtained from any source, including bacteria, protozoa, fungi, viruses, organelles, as well higher organisms such as plants or animals, particularly mammals, and more particularly humans. Other samples can be obtained from environmental sources (e.g., pond water, air sample), from man-made products (e.g., food), from forensic samples, and the like. Samples can be obtained from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples can be obtained from an embryo or from maternal blood. Samples can also be obtained from live or dead organisms or from in vitro cultures. Illustrative samples can include single cells, paraffin-embedded tissue samples, and needle biopsies.

The assays of the invention can be carried out on single cells or a population of cells (i.e., two or more cells). In some embodiments an assay is conducted using nucleic acids and proteins obtained from a single cell, or small number (fewer than 10, or fewer than 5) of cells. In one approach employing a single cell, the cell is isolated and lysed; and reagents, e.g., proximity extension probes, extension reagents, polymerases, amplification reagents are added directly to the lysate to perform the detection assay. In some embodiments, the assay, the isolation of macromolecules from single cells, or both are carried out using a microfluidic device. Microfluidic systems for isolating and obtaining macromolecules from single cells and/or conducting assays using the macromolecules are known. An exemplary device is the C1™ Single-Cell Auto Prep System which is commercially available from Fluidigm Corp. 7000 Shoreline Court, Suite 100, South San Francisco, Calif.). The C1™ Single-Cell Auto Prep System isolates single cells, lyses them, and carries out a series of reactions from the lysate (e.g., cDNA synthesis, nucleic acid amplification, etc.). Other devices are described in U.S. patent application Ser. No. 13/781,292 filed Feb. 28, 2013, entitled "Methods, Systems, And Devices For Multiple Single-Cell Capturing And Processing Using Microfluidics"; and U.S. Provisional Application No. 61/852,135 filed Mar. 15, 2013, entitled "Methods And Devices For Analysis Of Defined Multicellular Combinations," both of which are incorporated by reference in their entirety for all purposes. Optionally the C1™ Single-Cell Auto Prep System may be used in conjunction with Fluidigm's BioMark™ HD System (Fluidigm Corp. 7000 Shoreline Court, Suite 100, South San Francisco, Calif.). U.S. patent application Ser. No. 13/781,292 filed Feb. 28, 2013 is incorporated herein in its entirety all purposes.

Other devices for manipulation of single cells include the following (none of which are admitted to be prior art): Sims et al., 2007, "Analysis of single mammalian cells on-chip" Lab Chip 7:423-440; Wheeler et al., 2003, "Microfluidic device for single-cell analysis" Anal Chem 75:3581-3586; Skelley et al., 2009 "Microfluidic control of cell pairing and fusion" Nat Methods 6:147-152; Marcus et al., 2006, "Microfluidic single-cell mRNA isolation and analysis" Anal Chem 78:3084-3089; Bontoux et al., 2008 "Integrating whole transcriptome assays on a lab-on-a-chip for single cell gene profiling" Lab Chip 8:443-450; Zhong et al., 2008 "A microfluidic processor for gene expression profiling of single human embryonic stem cells" Lab Chip 8:68-74; Wheeler 2003 "Microfluidic Device for Single-Cell Analysis Anal. Chem." 75:3581-3586; and White et al., Aug. 23, 2011 "High-throughput microfluidic single-cell RT-qPCR PNAS" Vol. 108, 34:13999-14004; each of the aforelisted publications is incorporated herein by reference.

Additional methods for amplifying and detecting amplified products are described in U.S. Pat. Pub. Nos. 2012-0115143 ("Universal Probe Assay Methods"), US 2012-0288857 ("Multifunctional Probe-Primers"), US 2013-0045881 ("Probe Based Nucleic Acid Detection"); and copending commonly owned International Patent Application No. PCT/US2012/065376 ("NUCLEIC ACID DETECTION USING PROBES") and International POT Application No. PCT/US2007/063229 ("COOPERATIVE PROBES AND METHODS OF USING THEM"), each of which is expressly incorporated by reference for all purposes.

10. Kits

Kits according to the invention include one or more reagents useful for practicing one or more assay methods of the invention. A kit generally includes a package with one or more containers holding the reagent(s) (e.g., nucleic acid proximity extension probes and optionally, protein proximity extension probes), as one or more separate compositions. In some embodiments, the probes may be provided as an admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention, Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

The invention claimed is:

1. A method of detecting an RNA and a protein in a sample, the method comprising:
   (a) incubating a sample in a reaction mixture with a pair of protein-detecting proximity probes comprising a first and a second protein detecting proximity probe where:
      the first protein-detecting probe comprises a first antibody that binds to the target protein joined to a first polynucleotide that comprises an I segment at the 3' end that is complementary to an I segment on the 3' end of the second probe; and
      the second protein-detecting probe comprises a second antibody that binds to the target protein joined to a second polynucleotide that comprises an I segment complementary to the I segment at the 3' end of the first polynucleotide;
   wherein binding of the first antibody to the target protein and binding of the second antibody to the target protein allows the I segment of the first protein proximity probe to hybridize to the I segment of the second protein proximity probe to form a duplex;
   (b) extending the duplex using a DNA polymerase to provide an extended product
   (c) amplifying the extended product, or a subregion thereof, using a set of primers that amplify the extended product or subregion thereof; and
   (d) detecting an RNA of interest in the sample and the amount of amplicon from amplification of the extended product or subregion thereof.

2. The method of claim 1, wherein the sample is a single cell.

3. The method of claim 1, wherein the detecting step comprises a quantitative amplification reaction.

4. The method of claim 3, wherein the quantitative amplification reaction is qPCR.

5. The method of claim 1, wherein the DNA polymerase has 3' exonuclease activity.

6. The method of claim 1, wherein the amplification of step (c) is performed with a DNA polymerase different from the DNA polymerase employed in the extension reaction of step (b).

7. The method of claim 6, wherein the DNA polymerase in amplification reaction is a thermostable polymerase.

8. The method of claim 1, wherein the detecting step comprises a quantitative amplification reaction.

9. The method of claim 8, wherein the quantitative amplification reaction is qPCR.

10. The method of claim 1, wherein the detecting step comprises quantifying the amount of amplicon.

11. The method of claim 1, wherein detecting the RNA of interest in the sample comprises detecting an amplicon obtained by amplifying an extended product of a nucleic acid proximity extension reaction.

* * * * *